United States Patent
Hiroe

(10) Patent No.: US 8,173,022 B2
(45) Date of Patent: May 8, 2012

(54) METHOD FOR MANUFACTURING PACKING MATERIAL, PACKING MATERIAL, AND COLUMN

(75) Inventor: Yoshihisa Hiroe, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/255,277

(22) PCT Filed: Mar. 11, 2010

(86) PCT No.: PCT/JP2010/054119
§ 371 (c)(1),
(2), (4) Date: Sep. 8, 2011

(87) PCT Pub. No.: WO2010/104151
PCT Pub. Date: Sep. 16, 2010

(65) Prior Publication Data
US 2011/0315618 A1    Dec. 29, 2011

(30) Foreign Application Priority Data
Mar. 12, 2009 (JP) .................... 2009-059290

(51) Int. Cl.
*B01D 15/08* (2006.01)
(52) U.S. Cl. ............. 210/656; 210/635; 210/198.2; 210/502.1; 502/401; 502/439
(58) Field of Classification Search ................ 210/635, 210/656, 198.2, 502.1; 502/401, 402, 439
See application file for complete search history.

(56) References Cited

U.S. PATENT DOCUMENTS
3,808,125 A * 4/1974 Good ........................ 73/23.39
(Continued)

FOREIGN PATENT DOCUMENTS
JP    4-212058    8/1992
(Continued)

OTHER PUBLICATIONS
PTO Tranlation No. 12-1834 of Japan Patent No. 2005154197 dated Feb. 2012.*
(Continued)

*Primary Examiner* — Ernest G Therkorn
(74) *Attorney, Agent, or Firm* — IPUSA, PLLC

(57) ABSTRACT

A method for manufacturing a packing material includes a first step of reacting an inorganic particle having a hydroxyl group with a silane coupling agent including a silane coupling agent having an alkenyl group with a carbon number of 2 or more and 8 or less and/or an alkynyl group with a carbon number of 2 or more and 7 or less and a second step of reacting the inorganic particle having reacted with the silane coupling agent, with a compound represented by a general formula of:

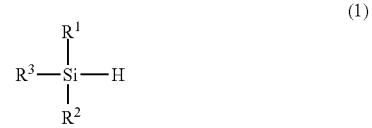

(1)

(in the formula, $R^1$ is an alkyl group with a carbon number of 4 or more and 50 or less or an aryl group with a carbon number of 6 or more and 30 or less and each of $R^2$ and $R^3$ is independently a hydrogen atom, a chloro group, or an alkyl group with a carbon number of 1 or more and 4 or less.).

1 Claim, 2 Drawing Sheets

U.S. PATENT DOCUMENTS

| | | | | |
|---|---|---|---|---|
| 3,878,092 | A | * | 4/1975 | Fuller ......................... 210/198.2 |
| 4,029,583 | A | * | 6/1977 | Chang et al. .................. 252/184 |
| 4,177,038 | A | * | 12/1979 | Biebricher et al. ............... 8/192 |
| 5,134,110 | A | | 7/1992 | Sudo et al. |
| 5,316,680 | A | * | 5/1994 | Frechet et al. ................ 210/635 |
| 5,318,848 | A | * | 6/1994 | Itoh et al. ..................... 428/405 |
| 5,522,994 | A | * | 6/1996 | Frechet et al. ................ 210/635 |
| 6,017,458 | A | * | 1/2000 | Ng et al. ....................... 210/635 |
| 6,994,791 | B2 | * | 2/2006 | Moller et al. ................. 210/656 |
| 7,223,473 | B2 | * | 5/2007 | Jiang et al. ................... 428/403 |
| 2003/0042203 | A1 | * | 3/2003 | Wormsbecher .............. 210/656 |
| 2004/0124149 | A1 | * | 7/2004 | Boschetti et al. ............. 210/656 |
| 2005/0242038 | A1 | * | 11/2005 | Chen ............................ 210/656 |
| 2006/0076296 | A1 | * | 4/2006 | Chen ............................ 210/656 |
| 2007/0090052 | A1 | * | 4/2007 | Broske et al. ................ 210/656 |
| 2009/0206034 | A1 | * | 8/2009 | Nakajima ..................... 210/635 |
| 2011/0257028 | A1 | * | 10/2011 | Gottschall ........................ 506/9 |

FOREIGN PATENT DOCUMENTS

| | | |
|---|---|---|
| JP | 2004-093360 | 3/2004 |
| JP | 2005-154197 | 6/2005 |
| JP | 2008-232802 | 10/2008 |
| WO | WO 2007/114144 | 10/2007 |

OTHER PUBLICATIONS

PTO Tranlation No. 12-1832 of Japan Patent No. 2004093360 dated Feb. 2012.*
Machine Language Tranlation of Japan Patent No. 2008-232802.*
International Search Report mailed on Jun. 15, 2010.

* cited by examiner

METHOD FOR MANUFACTURING PACKING MATERIAL, PACKING MATERIAL, AND COLUMN

REFERENCE TO RELATED APPLICATIONS

This application is a 371 of PCT/JP2010/54119 filed Mar. 11, 2010.

TECHNICAL FIELD

The present invention relates to a method for manufacturing a packing material, a packing material, and a column.

BACKGROUND ART

Conventionally, a silica gel with a surface on which a silanol group has been chemically modified by silylation with each kind of silane coupling agent has generally been used as a packing material for packing a column used in liquid chromatography. For a silane coupling agent, there is provided an octadecylchlorosilane compound, an octylchlorosilane compound, a butylchlorosilane compound, a cyanopropylchlorosilane compound, a phenylchlorosilane compound, or the like, and among these, an octadecylchlorosilane compound has been used most widely.

However, such a packing material has a large degree of an interaction with a polar substance, in particular, a basic substance, because a silanol group remains on a surface of a silica gel, and provides a problem of a large degree of peak tailing of a basic substance in a column.

Patent document 1 discloses a method of reacting an end cap agent with a silanol group remaining on a chemically modified silica gel or a porous glass at a reaction temperature at or above 250° C. in a gas phase.

However, even if such a method is used, a silanol group still remains on a surface of a silica gel or porous glass, and accordingly, it is desired that a peak tailing of a basic substance in a column is reduced.

Patent document 1: Japanese Patent Application Publication No. 4-212058

DISCLOSURE OF THE INVENTION

According to one aspect of the present invention, there is provided a method for manufacturing a packing material, including:

a first step of reacting an inorganic particle having a hydroxyl group with a silane coupling agent having an alkenyl group with a carbon number of 2 or more and 8 or less and/or an alkynyl group with a carbon number of 2 or more and 7 or less, and;

a second step of reacting the inorganic particle having reacted with the silane coupling agent, with a compound represented by a general formula of:

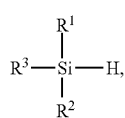
(1)

wherein $R^1$ is an alkyl group with a carbon number of 4 or more and 50 or less or an aryl group with a carbon number of 6 or more and 30 or less and each of $R^2$ and $R^3$ is independently a hydrogen atom, a chloro group, or an alkyl group with a carbon number of 1 or more and 4 or less.

According to another aspect of the present invention, there is provided a packing material manufactured by using the method for manufacturing a packing material as described above.

According to another aspect of the present invention, there is provided a column packed with the packing material as described above.

BEST MODE FOR CARRYING OUT THE INVENTION

Figure 1:
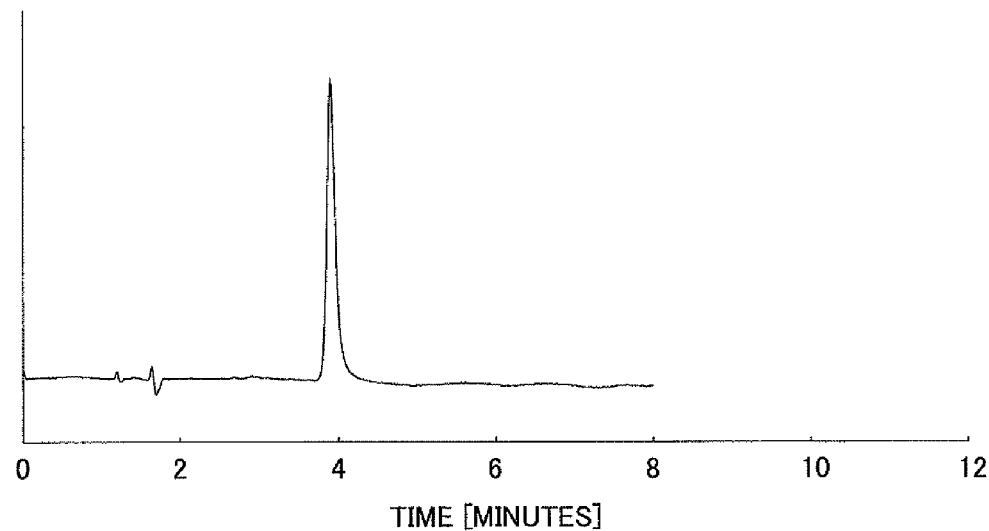
FIG. 1 is a diagram illustrating a measurement result of a tailing factor for a column packed with a packing material in practical example 1.

Next, an embodiment(s) for implementing the present invention will be described in conjunction with the drawings.

A method for manufacturing a packing material according to the present invention includes a first step of reacting an inorganic particle having a hydroxyl group with a silane coupling agent including a silane coupling agent having an alkenyl group with a carbon number of 2-8 and/or an alkynyl group with a carbon number of 2-7 (referred to as a first silane coupling agent, below) and a second step of reacting the inorganic particle having reacted with the silane coupling agent with a compound represented by a general formula of:

(1)

(in the formula, $R^1$ is an alkyl group with a carbon number of 4-50 or an aryl group with a carbon number of 6-30 and each of $R^2$ and $R^3$ is independently a hydrogen atom, a chloro group, or an alkyl group with a carbon number of 1-4). Because a silane coupling agent is thus reacted with an inorganic particle having a hydroxyl group before introducing an alkyl group with a carbon number of 4-50 or an aryl group with a carbon number of 6-30 onto a surface of the inorganic particle, it is possible to reduce an amount of a remaining hydroxyl group(s) near a surface of the inorganic particle. As a result, it is possible to obtain a packing material with a small degree of peak tailing of a basic substance.

If a first silane coupling agent has an alkenyl group with a carbon number of 9 or more and/or has an alkynyl group with a carbon number of 8 or more, reaction of a silane coupling agent with an inorganic particle having a hydroxyl group does not readily proceed due to steric hindrance.

If $R^1$ is an alkyl group with a carbon number of 3 or less in a compound represented by general formula (1), it is not possible to obtain a packing material with a small degree of peak tailing of a basic substance. Furthermore, if $R^1$ is an alkyl group with a carbon number of 51 or more or an aryl group with a carbon number of 31 or more, reaction of a compound represented by general formula (1) with an inorganic particle with an introduced alkenyl group with a carbon number of 2-8 and/or alkynyl group with a carbon number of 2-7 does not readily proceed due to steric hindrance. Moreover, if $R^2$ or $R^3$ is an alkyl group with a carbon number of 5 or more, reaction of a compound represented by general formula (1) with an inorganic particle with an introduced alkenyl group with a carbon number of 2-8 and/or alkynyl group with a carbon number of 2-7 does not readily proceed due to steric hindrance.

An inorganic particle having a hydroxyl group is not particularly limited and there is provided silica, titanium oxide, zinc oxide, zirconium oxide, aluminum oxide, a zeolite, or the like. Among these, a porous particle having a hydroxyl group such as that of a silica gel, a porous glass, a monolith silica, or the like is preferable.

An average particle size of an inorganic particle having a hydroxyl group is preferably 1-200 μm, and more preferably 3-50 μm. Furthermore, a pore size of an inorganic particle having a hydroxyl group is preferably 1-100 nm, and more preferably 4-50 nm. Moreover, a specific surface area of a porous an inorganic particle having a hydroxyl group is preferably 50-800 m$^2$/g, and more preferably 100-600 m$^2$/g.

In the specification and the claim(s) for the present application, an inorganic particle having a hydroxyl group includes an organic inorganic hybrid particle having a hydroxyl group such as a particle obtained by reacting a silane coupling agent having a hydroxyl group with an inorganic particle having a hydroxyl group.

For a compound represented by general formula (1), there is provided octadecyldimethylsilane or the like and two or more kinds thereof may be used in combination.

Although an inorganic particle having a hydroxyl group may be reacted with only a first silane coupling agent in a first step in the present invention, it is preferable to be reacted with a first silane coupling agent and a silane coupling agent having no alkenyl group or alkynyl group (referred to as a second silane coupling agent, below) because it is possible to control an amount of an introduced alkenyl group. Herein, it is more preferable that an inorganic particle having a hydroxyl group is reacted with a predetermined amount of a first silane coupling agent and subsequently reacted with an excessive amount of a second silane coupling agent. Thereby, it is possible to control an amount of an introduced alkenyl group and/or alkynyl group on a surface of an inorganic particle and to reduce an amount of a remaining hydroxyl group(s).

Additionally, an inorganic particle having a hydroxyl group may be reacted with a first silane coupling agent and/or a second silane coupling agent more than once in a first step.

A first silane coupling agent is not particularly limited, and there is provided a compound represented by a general formula of:

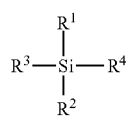

(2)

(in the formula, at least one of $R^1$, $R^2$, $R^3$, and $R^4$ is an alkenyl group with a carbon number of 2-8 or an alkynyl group with a carbon number of 2-7, at least one of $R^1$, $R^2$, $R^3$, and $R^4$ is a hydrogen atom, a halogen atom, a hydroxyl group, or an alkoxyl group with a carbon number of 1-4, and each of $R^1$, $R^2$, $R^3$, and $R^4$ except the ones above is independently a substituted or non-substituted alkyl group with a carbon number of 1-8, a substituted alkenyl group with a carbon number of 2-8, a substituted alkynyl group with a carbon number of 2-7, or a substituted or non-substituted aryl group with a carbon number of 6-12.), a compound represented by a general formula of:

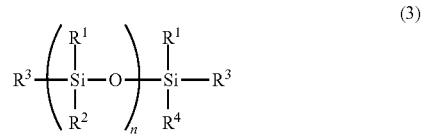

(3)

(in the formula, n is 1-100, at least one of $R^1$, $R^2$, $R^3$, and $R^4$ is an alkenyl group with a carbon number of 2-8 or an alkynyl group with a carbon number of 2-7, each of $R^1$, $R^2$, $R^3$, and $R^4$ except the one(s) above is independently a hydrogen atom, a halogen atom, a hydroxyl group, a vinyldimethylsiloxy group, an alkoxyl group with a carbon number of 1-4, a substituted or non-substituted alkyl group with a carbon number of 1-8, a substituted alkenyl group with a carbon number of 2-8, a substituted alkynyl group with a carbon number of 2-7, or a substituted or non-substituted aryl group with a carbon number of 6-12, and a plurality of $R^1$ and $R^3$ or $R^3$ in case where plural ones are present may be identical or different.), a compound represented by a general formula of:

(4)

(in the formula, n is 3-50, at least one of plural $R^1$ and $R^2$ is an alkenyl group with a carbon number of 2-8 or an alkynyl group with a carbon number of 2-7, each of $R^1$ and $R^2$ except the one(s) above is independently a hydrogen atom, a halogen atom, a hydroxyl group, an alkoxyl group with a carbon number of 1-4, a substituted or non-substituted alkyl group with a carbon number of 1-8, a substituted alkenyl group with a carbon number of 2-8, a substituted alkynyl group with a carbon number of 2-7, or a substituted or non-substituted aryl group with a carbon number of 6-12, and X is an oxy group or an imino group.), a compound represented by a general formula of:

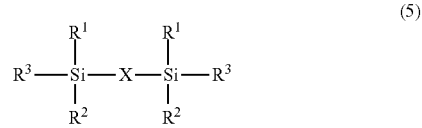

(5)

(in the formula, at least one of plural $R^1$, $R^2$, and $R^3$ is an alkenyl group with a carbon number of 2-8 or an alkynyl group with a carbon number of 2-7, each of $R^1$, $R^2$, and $R^3$ except the one(s) above is independently a hydrogen atom, a halogen atom, a hydroxyl group, an alkoxyl group with a carbon number of 1-4, a substituted or non-substituted alkyl group with a carbon number of 1-8, a substituted alkenyl group with a carbon number of 2-8, a substituted alkynyl group with a carbon number of 2-7, or a substituted or non-substituted aryl group with a carbon number of 6-12, X is a single bond, an imino group, or a group represented by a general formula of:

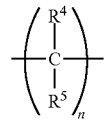

(in the formula, each of $R^4$ and $R^5$ is independently a hydrogen atom or a trimethylsiliy group, and n is an integer of 1-8).), 1,1-bis(trimethoxysilylmethyl)ethylene, or the like, wherein two or more kinds thereof may be used in combination.

Additionally, an alkenyl group with a carbon number of 2-8 or an alkynyl group with a carbon number of 2-7 in general formulas (2)-(5) is not particularly limited as long as hydrosilylation reaction with a compound represented by general formula (1) is allowed, and there is provided a vinyl group, an ethynyl group, or the like. Furthermore, a halogen group is not particularly limited as long as a condensation reaction with a hydroxyl group possessed by an inorganic particle is allowed, and there is provided a chloro group, a bromo group, an iodo group, or the like. Moreover, a substituent for an alkyl group, alkenyl group, alkynyl group, or aryl group is not particularly limited as long as the substituent does not inhibit reaction, and there is provided a cyano group, a hydroxyl group, a carboxyl group, an amide group, an imide group, a sulfa group, an amino group, a glyceroyl group, or the like.

For a compound represented by general formula (2), there is provided vinyltrichlorosilane, vinyltrimethoxysilane, vinyltriethoxysilane, vinyltriisopropoxysilane, vinyltriphenoxysilane, vinylphenylmethylsilane, vinylphenylmethylchlorosilane, vinylphenyldiethoxysilane, vinylphenyldichlorosilane, vinyldiphenylchlorosilane, vinyldiphenylethoxysilane, vinyloctyldichlorosilane, vinyldimethylsilane, vinyldimethylchlorosilane, divinyldichlorosilane, trivinylchlorosilane, trivinylmethoxysilane, trivinylethoxysilane, trivinylsilane, or the like.

For a compound represented by general formula (3), there is provided 1,5-divinyl-3,3-diphenyl-1,1,5,5-tetramethyltrisiloxane, or the like.

For a compound represented by general formula (4), there is provided 1,3,5-trivinyl-1,3,5-trimethylcyclotrisiloxane, 1,3,5-trivinyl-1,3,5-trimethylcyclotrisilazane, or the like.

For a compound represented by general formula (5), there is provided 1,3-divinyltetramethyldisiloxane, 1,3-divinyltetramethyldisilazane, or the like.

A second silane coupling agent is not particularly limited, and there is provided a compound represented by a general formula of:

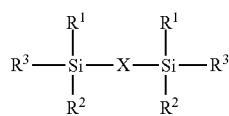

(6)

(in the formula, each of $R^1$, $R^2$, and $R^3$ is independently an alkyl group with a carbon number of 1-9 and X is a single bond or an imino group.), a compound represented by a general formula of:

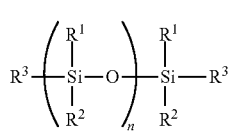

(7)

(in the formula, n is 0-50, 1-3 of plural $R^1$, $R^2$, and $R^3$ is/are a hydrogen atom(s) or an alkoxy group(s) with a carbon number of 1-4, and each of $R^1$, $R^2$, and $R^3$ except one(s) above is independently an alkyl group with a carbon number of 1-9.), a compound represented by a general formula of:

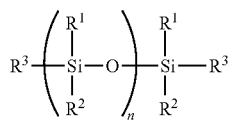

(8)

(in the formula, n is 1-50, and each of $R^1$, $R^2$, and $R^3$ is independently an alkyl group with a carbon number of 1-9.), a compound represented by a general formula of:

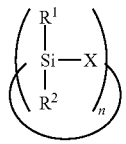

(9)

(in the formula, n is 3-10, each of $R^1$ and $R^2$ is independently an alkyl group with a carbon number of 1-9, and X is an oxy group or an imino group.), or the like, wherein two or more kinds thereof may be used in combination.

For a compound represented by general formula (6), there is provided hexamethyldisilane, hexamethyldisilazane, or the like.

For a compound represented by general formula (7), there is provided dimethyldimethoxysilane, diethylmethylsilane, triethylsilane, trimethylmethoxysilane, 1,1,3,3-tetramethyldisiloxane, 1,1,3,3,5,5-hexamethyltrisiloxane, 1,3-dimethoxytetramethyldisiloxane, or the like.

For a compound represented by general formula (8), there is provided hexamethyldisiloxane, tetradecamethylhexasiloxane, or the like.

For a compound represented by general formula (9), there is provided hexamethylcyclotrisiloxane, octamethylcyclotetrasiloxane, decamethylcyclopentasiloxane, dodecamethylcyclohexasiloxane, hexamethylcyclotrisilazane, or the like.

When an inorganic particle having a hydroxyl group is reacted with a silane coupling agent in the present invention, it is possible to use a publicly-known method, and for example, reaction is conducted at 0-400° C. for 30 minutes-72 hours under the presence of a solvent such as toluene.

Furthermore, when an inorganic particle having reacted with a silane coupling agent is reacted with a compound represented by general formula (1) in a second step, it is possible to use a publicly-known method, and for example, reaction is conducted at 50-300° C. for 2 hours or more under the presence of a solvent such as toluene. For a catalyst, it is possible to use a ruthenium, rhodium, palladium, osmium, iridium, or platinum compound, wherein a palladium compound or a platinum compound is preferable. A palladium compound is not particularly limited, and there is provided palladium (II) chloride, ammonium tetramminechloropalladate (II), palladium (II) oxide, palladium (II) hydroxide, or the like. A platinum compound is not particularly limited, and there is provided platinum (II) chloride, tetrachloroplatinic (II) acid, platinum (IV) chloride, hexachloroplatinic (IV) acid, ammonium hexachloroplatinate (IV), platinum (II) oxide, platinum (II) hydroxide, platinum (IV) dioxide, platinum (IV) oxide, platinum (IV) disulfide, platinum (IV) sulfide, potassium hexachloroplatinate (IV), or the like.

Additionally, a silanol group remaining on an inorganic particle and originating from a silane coupling agent may be blocked by using a publicly-known method after a second step.

Because a column according to the present invention is packed with a packing material manufactured by using a method for manufacturing a packing material according to the present invention, it is possible to provide a small degree of peak tailing of a basic material, and specifically, it is possible for a tailing factor of amitriptyline to be 0.9-2.0. Additionally, it is possible to apply a column according to the present invention to liquid chromatography and it is possible to analyze or fractionate a sample.

A practical example(s) for the present invention will be further described in detail below. Additionally, the present invention is not limited thereto.

Practical Example 1

1 g of a silica gel with an average particle size of 5 μm and a specific surface area of 450 mm$^2$/g was charged into an ampoule and dried at 120° C. and a reduced pressure for 10 hours. After the ampoule was cooled, addition of 0.55 mL of vinylmethyldimethoxysilane and sealing thereof were conducted under nitrogen atmosphere and reaction was conducted at 350° C. for 12 hours. Furthermore, after a product was taken out and washed with 10 mL of chloroform and 10 mL of methanol, drying was conducted at 120° C. and a reduced pressure for 10 hours.

After 0.7 g of obtained particles were dispersed in 3 mL of dehydrated toluene, addition of 3.1 mL of octadecyldimethylsilane and stirring were conducted. Then, after 14.45 μL of 3 mass % solution of chloroplatinic acid in toluene was added and reaction was conducted at 70° C. for 8 hours, cooling and filtration were conducted. After an obtained residue was washed with 10 mL of chloroform and 10 mL of methanol, drying was conducted at 120° C. and a reduced pressure for 10 hours to obtain a packing material.

Practical Example 2

15 g of a silica gel with an average particle size of 5 μm and a specific surface area of 450 mm$^2$/g was dispersed in 60 mL of dehydrated toluene. Then, after addition of 5.79 mL of pyridine and 3.12 mL of vinyltrichlorosilane and heating and reflux for 3 hours were conducted, cooling and filtration were conducted. An obtained residue was washed with 100 mL of toluene, 100 mL of acetonitrile, and 100 mL of 60 mass % aqueous solution of acetonitrile. Furthermore, dispersion in 100 mL of 60 mass % aqueous solution of actonitrile, stirring at room temperature for 1.5 hours, and filtration were conducted. After an obtained residue was washed with 100 mL of 60 mass % of acetonitrile and 100 mL of methanol, drying at 120° C. and a reduced pressure for 10 hours was conducted. The content of carbon in obtained particles was 4.00 mass %.

2 g of obtained particles were charged in an ampoule and drying at 120° C. and a reduced pressure for 10 hours was conducted. After the ampoule was cooled, addition of 0.416 mL of dimethyldimethoxysilane and sealing thereof were conducted under nitrogen atmosphere, and reaction was conducted at 350° C. for 6 hours. Furthermore, after a product was taken out and washed with 20 mL of chloroform and 20 mL of methanol, drying at 120° C. and a reduced pressure for 10 hours was conducted.

After 0.7 g of obtained particles were dispersed in 3 mL of dehydrated toluene, addition of 3.1 mL of octadecyldimethylsilane and stirring were conducted. Then, after addition of 14.45 μL of 3 mass % solution of chloroplatinic acid in toluene and reaction at 70° C. for 8 hours were conducted, cooling and filtration were conducted. After an obtained residue was washed with 10 mL of chloroform and 10 mL of methanol, drying at 120° C. and a reduced pressure for 10 hours was conducted to obtain a packing material.

Comparative Example 1

After 10 g of a silica gel was dried at 120° C. and a reduced pressure for 10 hours, cooling and dispersion in 40 mL of dehydrated toluene were conducted. Then, after addition of 0.80 mL of pyridine and 3.3 mL of octadecyldimethylchlorosilane and heating and reflux for 3 hours were conducted, cooling and filtration were conducted. After an obtained residue was washed with 100 mL of toluene, 100 mL of chloroform, and 100 mL of methanol, drying at 120° C. and a reduced pressure for 10 hours was conducted.

5 g of obtained particles were charged into an ampoule and drying at 120° C. and a reduced pressure for 10 hours was conducted. After an ampoule was cooled, addition of 1.0 mL of hexamethylsilazane and sealing thereof were conducted under nitrogen atmosphere and reaction at 250° C. for 6 hours was conducted. Furthermore, after a product was taken out and washed with 50 mL of chloroform and 100 mL of methanol, drying at 120° C. and a reduced pressure for 10 hours was conducted to obtain a packing material.

[Measurement of Tailing Factors]

After columns were packed with packing materials in practical example 1, practical example 2, and comparative example 1, a mobile phase with 20 mM phosphate buffer: acetonitrile being 60:40 (volume ratio) was used to measure tailing factors of amitriptyline as a basic substance.

Figure 2:
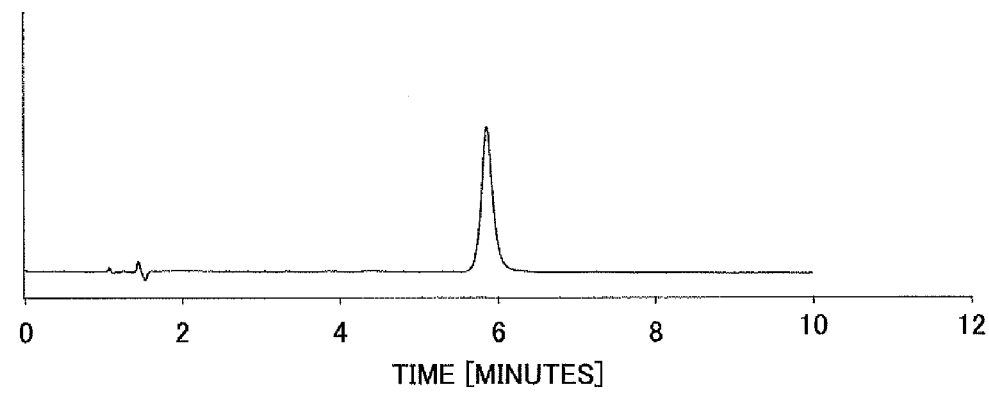
FIG. 2 is a diagram illustrating a measurement result of a tailing factor for a column packed with a packing material in practical example 2.
Figure 3:
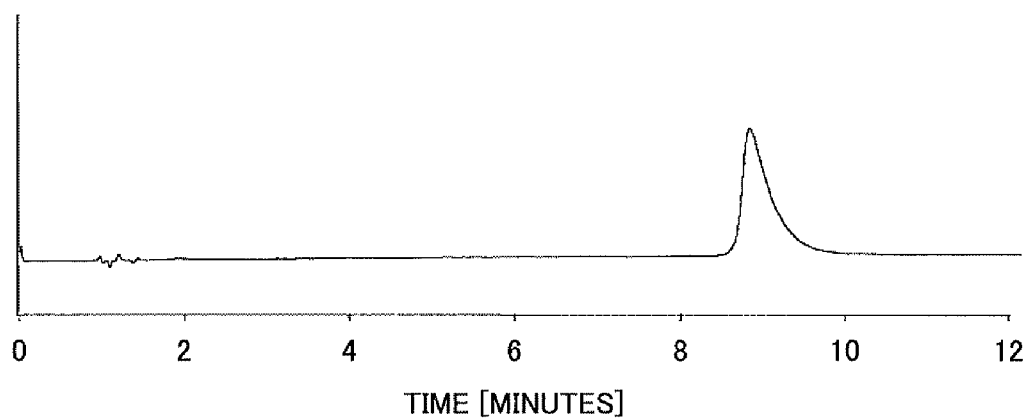
FIG. 3 is a diagram illustrating a measurement result of a tailing factor for a column packed with a packing material in comparative example 1.

FIG. 1, FIG. 2, and FIG. 3 illustrate measurement results of the tailing factors for the columns packed with the packing materials in practical example 1, practical example 2, and comparative example 1. Herein, the tailing factor and number of theoretical plates for the column packed with the packing material in practical example 1 were 1.39 and 6313, respectively, and the tailing factor and number of theoretical plates for the column packed with the packing material in practical example 2 were 1.15 and 7814, respectively. On the other hand, the tailing factor and number of theoretical plates for the column packed with the packing material in comparative example 1 were 2.19 and 3292, respectively.

APPENDIX

At least one embodiment of the present invention is intended to provide a method for manufacturing a packing material which is capable of manufacturing a column in which a small degree of peak tailing of a basic substance is provided, a packing material which is manufactured by using the method for manufacturing a packing material, and a column packed with the packing material, while taking a problem possessed by the aforementioned conventional art into consideration.

The invention as described in embodiment (1) is a method for manufacturing a packing material characterized by including a first step of reacting an inorganic particle having a hydroxyl group with a silane coupling agent including a silane coupling agent having an alkenyl group with a carbon number of 2 or more and 8 or less and/or an alkynyl group with a carbon number of 2 or more and 7 or less, and a second step of reacting the inorganic particle having reacted with the silane coupling agent, with a compound represented by a general formula of:

(1)

(in the formula, R is an alkyl group with a carbon number of 4 or more and 50 or less or an aryl group with a carbon number of 6 or more and 30 or less and each of $R^2$ and $R^3$ is independently a hydrogen atom, a chime group, or an alkyl group with a carbon number of 1 or more and 4 or less.).

The invention as described in embodiment (2) is the method for manufacturing a packing material as described in embodiment (1), characterized in that the first step includes a step of reacting the inorganic particle with the silane coupling agent having an alkenyl group with a carbon number of 2 or more and 8 or less and/or an alkynyl group with a carbon number of 2 or more and 7 or less and a step of reacting the inorganic particle having reacted with the silane coupling agent, with a silane coupling agent having no alkenyl group or alkynyl group.

The invention as described in embodiment (3) is a packing material characterized by being manufactured by using the method for manufacturing a packing material as described in embodiment (1) or (2).

The invention as described in embodiment (4) is a column characterized by being packed with the packing material as described in embodiment (3).

The invention as described in embodiment (5) is the column as described in embodiment (4) characterized in that a tailing factor of amitriptyline is 0.9 or more and 2.0 or less.

According to at least one embodiment of the present invention, it is possible to provide a method for manufacturing a packing material which is capable of manufacturing a column in which a small degree of peak tailing of a basic substance is provided, a packing material which is manufactured by using the method for manufacturing a packing material, and a column packed with the packing material.

The present international application claims its priority based on Japanese Patent Application No. 2009-059290 filed on Mar. 12, 2009, and the entire content of Japanese Patent Application No. 2009-059290 is incorporated by reference in the present international application.

The invention claimed is:

1. A packing material manufactured by using a method for manufacturing a packing material, comprising:
   a first step of reacting an inorganic particle having a hydroxyl group with a silane coupling agent having an alkenyl group with a carbon number of 2 or more and 8 or less and/or an alkenyl group with a carbon number of 2 or more and 7 or less, and an additional step of reacting the inorganic particle having reacted with the silane coupling agent with a silane coupling agent having no alkenyl group or alkynl group, and;
   a second step of reacting the inorganic particle having reacted with the silane coupling agent with a compound represented by a general formula (1) of:

(1)

wherein $R^1$ is an alkyl group with a carbon number of 4 or more and 50 or less or an aryl group with a carbon number of 6 or more and 30 or less and each of $R^2$ and $R^3$ is independently a hydrogen atom, a chloro group, or an alkyl group with a carbon number of 1 or more and 4 or less.

* * * * *